US00PP25471P3

(12) United States Plant Patent
Kardos

(10) Patent No.: US PP25,471 P3
(45) Date of Patent: Apr. 28, 2015

(54) *LOROPETALUM CHINENSE* VAR. *RUBRUM* PLANT NAMED 'PIILC-III'

(50) Latin Name: ***Loropetalum chinense* var. *rubrum***
Varietal Denomination: PIILC-III

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 13/694,994

(22) Filed: Jan. 23, 2013

(65) Prior Publication Data

US 2014/0208470 P1 Jul. 24, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

| | | | |
|---|---|---|---|
| PP16,615 | P2 | 6/2006 | Griffith |
| PP18,331 | P2 | 12/2007 | Meadows |
| PP18,441 | P2 | 1/2008 | Berry |

*Primary Examiner* — Kent L Bell
(74) *Attorney, Agent, or Firm* — Lathrop & Gage LLP

(57) ABSTRACT

A new and distinct cultivar of *Loropetalum chinense* var. *rubrum* plant named 'PIILC-III', characterized by its compact, mounded, spreading growth habit; dark purple foliage color that persists through summer and winter; dark pink flowers in spring; and improved cold hardiness compared to other compact purple-leaf cultivars.

3 Drawing Sheets

Genus and species of plant claimed: *Loropetalum chinense* var. *rubrum*.

Variety denomination: 'PIILC-III'.

BACKGROUND OF THE INVENTION

The present invention relates to a new and distinct cultivar of *Loropetalum chinense* var. *rubrum*, a member of the Hamamelidaceae family, hereinafter referred to by its cultivar name 'PIILC-III'. This cultivar is grown primarily as an ornamental for landscape use and for use as a potted plant.

The cultivar originated from an open-pollination of *Loropetalum chinense* var. *rubrum* 'GriffCRL' (U.S. Plant Pat. No. 16,615) in Watkinsville, Ga. in 2008, and was selected from the progeny seedlings of this open-pollination by continued evaluation for growth habit and improved foliage characteristics. The cultivar 'PIILC-III' originated and was discovered in a cultivated environment in an outdoor nursery in Watkinsville, Ga.

'PIILC-III' has been asexually reproduced by softwood cuttings since 2009 in Watkinsville, Ga. The characteristics of the cultivar have been stable and reproduced true to type in successive vegetative generations.

SUMMARY OF THE INVENTION

'PIILC-III' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIILC-III' from all other varieties in commerce known to the inventor.

1) Compact, mounded, spreading growth habit.
2) Dark purple foliage color that persists through summer and winter.
3) Dark pink flowers in spring.
4) Improved cold hardiness compared to other compact purple-leaf cultivars.

'PIILC-III' is distinguished from its female parent 'GriffCRL' by its growth habit foliage color, and flower color. 'PIILC-III' has a compact mounded, spreading growth habit reaching 107 cm high×213 cm wide after 4½ years, whereas 'GriffCRL' has an overall larger, rounded growth habit reaching approximately 274 to 335 cm high and wide in the same amount of time. 'PIILC-III' has dark purple foliage that persists through summer and winter, whereas 'GriffCRL' has duller red-purple foliage that will become greenish purple in summer and winter. 'PIILC-III' has dark pink flowers, whereas 'GriffCRL' has light pink flowers. There are no other cultivars of *Loropetalum chinense* var. *rubrum* with this combination of traits known to the inventor.

'PIILC-III' can be compared to the cultivar 'PIILC-I' (U.S. Plant patent application Ser. No. 13/694,190), but differs in foliage and flower color. 'PIILC-III' has dark purple foliage, whereas 'PIILC-I' has rich reddish purple foliage. 'PIILC-III' has dark pink flowers, whereas 'PIILC-I' has bright pink flowers.

'PIILC-III' can be compared to the cultivar 'Peack' (U.S. Plant Pat. No. 18,441), but differs in growth habit, overall size, vigor, and hardiness. 'PIILC-III' has a compact mounded, spreading growth habit reaching 107 cm×213 cm after 4½ years, whereas 'Peack' has a mounding and weeping habit reaching 46 cm×92 cm after 3 years. 'PIILC-III' is more vigorous than 'Peack'. 'PIILC-III' has exhibited increased cold hardiness compared to 'Peack' in Zone 7.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Loropetalum*.

DETAILED DESCRIPTION

Figure 1:
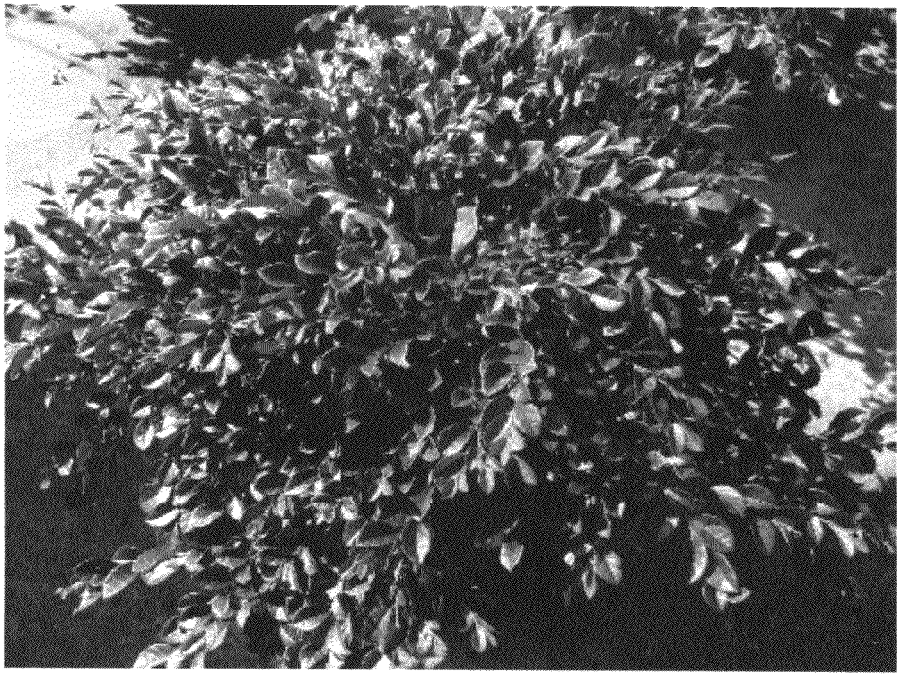
FIG. 1 illustrates the growth habit of a 'PIILC-III' plant growing in a container.
Figure 2:
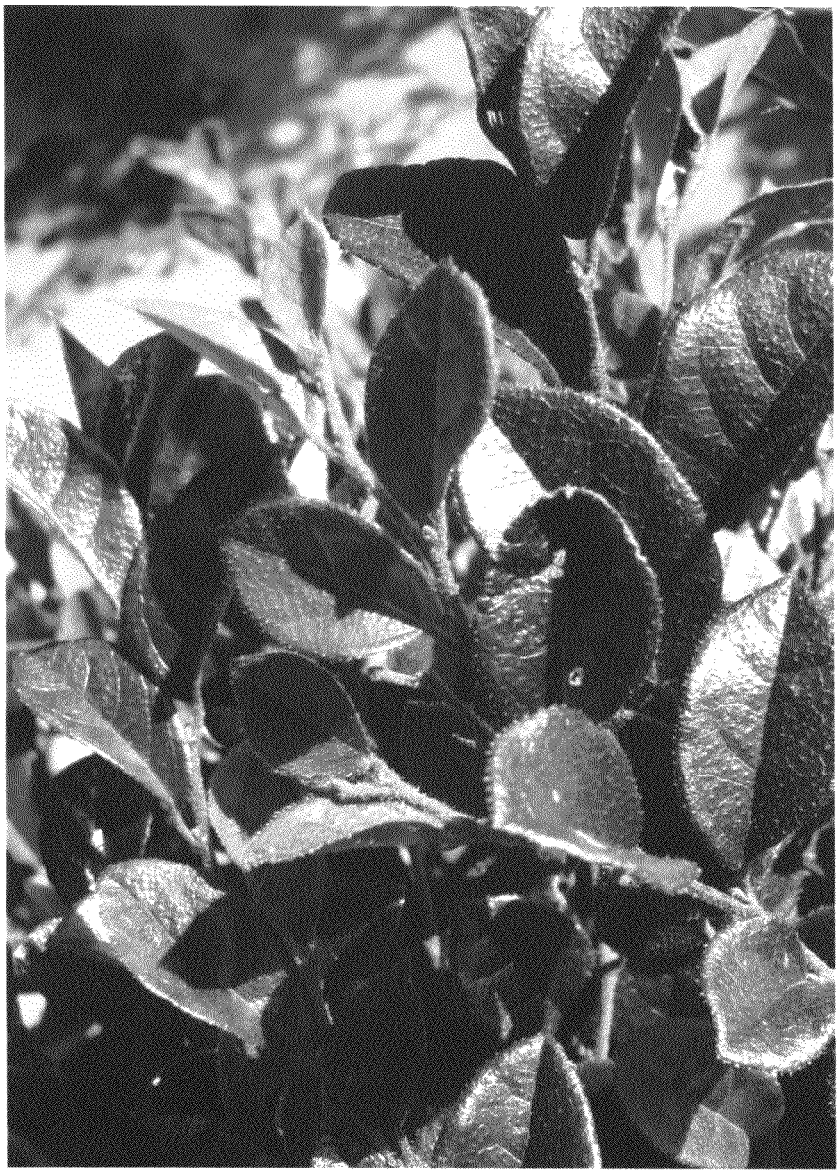
FIG. 2 illustrates a close-up of the foliage of 'PIILC-III'.
Figure 3:
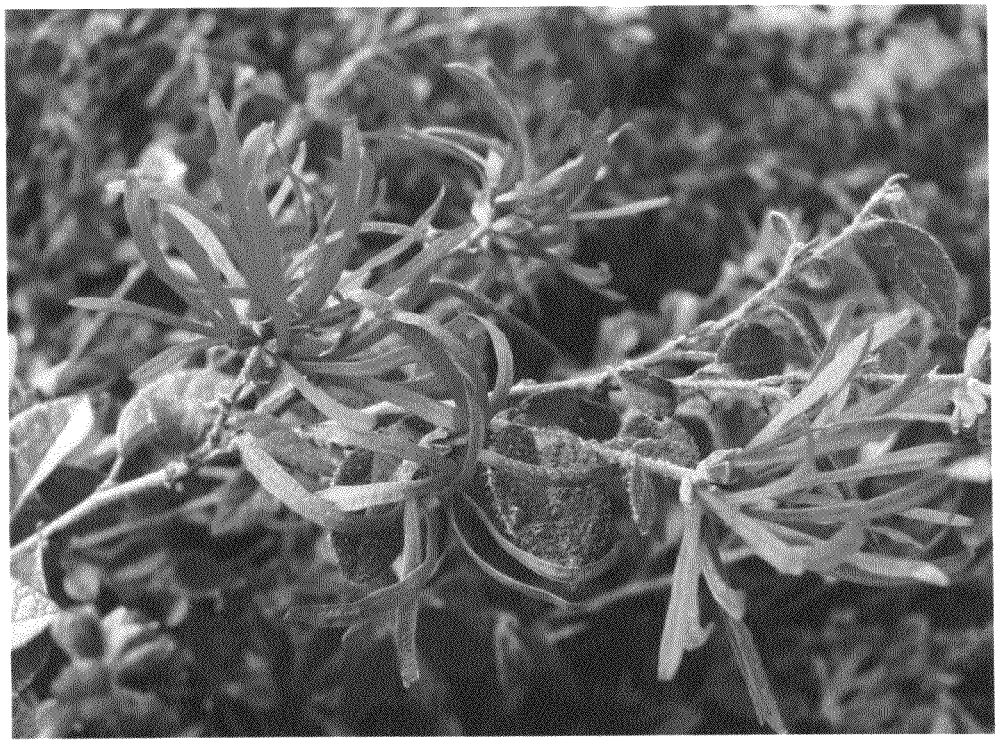
FIG. 3 illustrates a close-up of the flowers of 'PIILC-III'

In the following description, color references are made to The Royal Horticultural Society Colour Chart, 2007 Edition, except where general terms of ordinary dictionary significance are used. Plants used for the description were approximately 2½ years old and were grown in 11.8 L containers under outdoor conditions in Watkinsville, Ga. Colors are described using The Royal Horticultural Society Colour Chart (R.H.S.).

Botanical classification: *Loropetalum chinense* var. *rubrum* 'PIILC-III'.

Parentage:

*Female, or seed, parent.*—*Loropetalum chinense* var. *rubrum* 'GriffCRL' (U.S. Plant Pat. No. 16,615).

*Male, or pollen, parent.*—Unknown (open-pollinated).

Propagation: Type cutting: terminal cuttings.

*Time to initiate roots, summer.*—About 35 days at 32° C.

Plant description: Flowering shrub; compact, mounded, spreading growth habit. Freely branching; pruning enhances lateral branch development.

*Root description.*—Numerous, fine, fibrous and well-branched.

*Plant size.*—The original plant, now about 4½-years-old in the ground, is about 107 cm in height from the soil level to the top of the foliage, and about 213 cm in diameter. First year stems have a length of 20.32 cm to 25.4 cm. First year stems have a diameter of about 1.5 mm. Shape: round. Color: N186A. Pubescence: heavily stellate. Second year stems have a length of 30.48 cm to 45.72 cm. Second year and older stems have a diameter of about 3 mm or more. Shape: round. Color: N200A. Pubescence: none.

*Trunk diameter.*—About 2.8 cm at the soil line. Color: 199A.

*Internode length.*—About 1.5 cm.

*Strength.*—Flexible when young, more easily broken once mature.

*Bark.*—Exfoliates in flakes beginning on second or third year stems.

Vegetative buds: Alternate in arrangement, imbricate, with stellate pubescence.

*Color.*—187B.

*Size.*—About 1 mm in length and 1 mm in width.

Foliage description:

*Arrangement.*—Alternate, simple.

*Length.*—About 3.1 cm.

*Width.*—About 2 cm.

*Shape.*—Ovate-rounded.

*Apex.*—Pointed.

*Base.*—Oblique.

*Margin.*—Finely toothed.

*Texture (upper and lower surfaces).*—Stellate or sandpaper like pubescence.

*Venation pattern.*—Pinnate.

*Venation color in developing foliage (upper surface).*—N186C.

*Venation color in developing foliage (lower surface).*—N77B.

*Venation color in fully expanded foliage (upper surface).*—N186A.

*Venation color in fully expanded foliage (lower surface).*—N77C.

*Color in developing foliage (upper surface).*—N186C.

*Color in developing foliage (lower surface).*—N77B.

*Color in fully expanded foliage (upper surface).*—N186A.

*Color in fully expanded foliage (lower surface).*—N77C.

*Petiole length.*—About 3.5 mm.

*Petiole diameter.*—About 1 mm.

*Petiole color.*—N186C.

*Pubescence.*—Stellate.

Flower description: Flowers are produced in April in Watkinsville, Ga. and sporadically until frost. An inflorescence is showy for about two weeks, and individual flowers last about two to three days and are self-cleaning. Fragrance: none.

*Inflorescence type.*—Umbel produced from leaf axils and terminally.

*Inflorescence shape.*—Four to five strap-like petals forming a lose funnel.

*Inflorescence diameter.*—2.5 to 3.5 cm.

*Inflorescence depth.*—1.8 cm.

*Number of florets per inflorescence.*—4-8.

*Sepals.*—Arrangement: opposite. Number: 4. Shape: ovate. Margin: entire. Apex: acute to obtuse turning outward. Base: fused onto calyx cup. Length: 0.32 cm. Width: 0.2 cm. Texture: pubescent. Color: upper surface — 64A; lower surface — 59A.

*Peduncle.*—About 8 mm in length, about 1 mm in diameter, color is N186C, with stellate pubescence.

*Flower buds.*—Shape: orbicular. Length: about 4 mm. Diameter: about 2 mm. Four to eight flowers from globose heads on branchlet terminals. Color: 185B.

*Calyx.*—About 3.5 mm in length, about 2 mm in diameter, color 185B, for both surfaces, with stellate pubescence.

Petals:

*Arrangement/appearance.*—4 per flower.

*Petal length.*—About 1.7 cm.

*Petal width.*—About 1 mm.

*Petal shape.*—Strap-shaped.

*Petal apex.*—Acuminate.

*Petal margin.*—Entire.

*Texture.*—Smooth.

*Petal base.*—Obtuse.

*Petal color.*—Upper and lower surfaces are 59C.

Stamens:

*Quantity/arrangement.*—4 or 5 stamens, 1.5 mm long, 0.3 mm in width, and N77A in color.

*Pollen.*—Produced in very small quantities and is 158A in color.

Pistils:

*Quantity*.—One or two inferior pistils per flower.

*Pubescence*.—None.

*Pistil length*.—About 2 mm in length.

*Pistil color*.—71A.

*Stigma*.—Rounded, 71A in color.

*Style*.—1 mm in length and 71A in color.

*Ovary*.—1 mm in length, 1 mm in diameter, and N80A in color.

Plant hardiness:

*Plant hardiness*.—USDA Plant Hardiness Zone Map (2012): Zone 7 to 9.

Disease/pest resistance: Plant of the claimed *Loropetalum* cultivar grown in the garden have not been noted to be susceptible or resistant to pathogens and pests common to *Loropetalum*.

Fruit: None observed to date.

I claim:

1. A new and distinct *Loropetalum chinense* var. *rubrum* plant named 'PIILC-III', substantially as illustrated and described herein.

* * * * *